US008865749B2

(12) United States Patent
Marshall

(10) Patent No.: US 8,865,749 B2
(45) Date of Patent: Oct. 21, 2014

(54) TREATMENT AND PREVENTION OF TH1 AND 'AUTOIMMUNE' DISEASES EFFECTED WITH ANTIBIOTICS AND/OR ANGIOTENSIN INHIBITION

(76) Inventor: Trevor Gordon Marshall, Thousand Oaks, CA (US)

( * ) Notice: Subject to any disclaimer, the term of this patent is extended or adjusted under 35 U.S.C. 154(b) by 1647 days.

(21) Appl. No.: 11/161,318

(22) Filed: Jul. 29, 2005

(65) Prior Publication Data

US 2006/0025358 A1 Feb. 2, 2006

Related U.S. Application Data

(60) Provisional application No. 60/522,007, filed on Aug. 1, 2004.

(51) Int. Cl.
| A61K 31/41 | (2006.01) |
| A61K 31/335 | (2006.01) |
| A61K 31/65 | (2006.01) |
| A61K 31/704 | (2006.01) |

(52) U.S. Cl.
CPC ............... *A61K 31/65* (2013.01); *A61K 31/704* (2013.01)
USPC .......................................... 514/359; 514/463

(58) Field of Classification Search
USPC ................................................. 514/359, 463
See application file for complete search history.

(56) References Cited

U.S. PATENT DOCUMENTS

| 5,563,130 | A | 10/1996 | Backer et al. |
| 2003/0083339 | A1 | 5/2003 | Tamura |
| 2003/0181406 | A1 | 9/2003 | Schetter et al. |
| 2003/0199424 | A1 | 10/2003 | Smith ............................... 514/1 |
| 2003/0207819 | A1* | 11/2003 | Moskowitz |
| 2004/0097565 | A1 | 5/2004 | Terashita ...................... 514/364 |
| 2004/0138187 | A1 | 7/2004 | Reading et al. |
| 2004/0219208 | A1* | 11/2004 | Kawamura et al. ........... 424/468 |
| 2005/0112638 | A1 | 5/2005 | Sandberg ......................... 435/6 |
| 2005/0119323 | A1 | 6/2005 | Kubota et al. |
| 2006/0135422 | A1* | 6/2006 | Moskowitz ..................... 514/12 |
| 2007/0135504 | A1 | 6/2007 | Marshall |
| 2007/0149452 | A1 | 6/2007 | Marshall |

OTHER PUBLICATIONS

Merck Manual, Sixteenth edition, 1992, p. 1083.*
St. Clair et al., The Effets of Intravenous Doxycycline Therapy for Rheumatoid Arthritis. May 2001, Arthritis & Rheumatism, vol. 44, No. 5, pp. 1043-1047.*
Eichenfield. Minocyline and autoimmunity. 1999, current Opinion in Pediatrics, 11: 447-456.*
Albert, P. J. et al. (2009). "Vitamin D: The Alternative Hypothesis," *Autoimmunity Reviews*, Article in Press, 6 pages.
Blaney, G. P. et al. (Submitted Jan. 9, 2009). "Vitamin D Metabolites as Clinical Markers in Autoimmune and Chronic Disease," *Annals of The New York Academy of Sciences*, unedited manuscript, 14 pages.
Marshal, T. G. et al. (2004). "Antibacterial Therapy Induces Remission in Sarcoidosis," English translation of *MKDTS* paper, pp. 1-9.
Marshal, T. G. et al. (2004). "Sarcoidosis Succumbs to Antibiotics—Implications for Autoimmune Disease," *Autoimmunity Reviews*, 3:295-300.
Marshall, T. (Apr. 18, 2009). Written transcript of "The Marshall Protocol in a Clinical Environment: Observations from the Initial Cohort" presented at Workshop on Chlamydial Infection, Prague, Czech Republic, 12 pages.
Marshall, T. (Dec. 5-7, 2008). Written transcript of "Understanding Human Disease Requires Study of a Metagenome, Not Just the Human Genome" Keynote Speech at 2008 World Gene Congress, Foshan, China, located at <http://autoimmunityresearch.org/transcripts/WCG2008_Keynote_Transcript.pdf>. (12 pages).
Marshall, T. G. et al. (Apr. 2004). "Putative Antibacterial Mechanisms for Angiotensin II Receptor Blockers," *Journal of Independent Medical Research*, located at <http://www.joimr.org/marshall-vol2-no2.pdf>, 2(2):10 pages.
Marshall, T. G. et al. (Aug. 2, 2003). "Antibiotics in Sarcoidosis—Reflections on the First Year," *Journal of Independent Medical Research*, located at <http://www.joimr.org/marshall-vol1-no3-B.pdf>, 1(5):1-8.

(Continued)

*Primary Examiner* — Renee Claytor
(74) *Attorney, Agent, or Firm* — Morrison & Foerster LLP

(57) ABSTRACT

This invention is a method of killing the stealthy intra-cellular bacteria which cause many Th1 and 'Autoimmune' diseases. The methods described in this invention will treat and prevent the diseases customarily named Diabetes Type 1, Diabetes Type 2, Rheumatic Arthritis, Reactive Arthritis, Osteo Arthritis, Psoriasis, Scleroderma, Osteoporosis, Atherosclerosis, Myocarditis, Endocarditis, Pericarditis, Alzheimer's, Cystic Fibrosis, Hashimoto's Thyroiditis, Graves Disease, Leprosy, Syphilis, Lyme, Chronic Lyme, Borreliosis, Neuro-borreliosis, Inflammatory Bowel Disease (IBD), Tuberculosis, Latent Tuberculosis, Sarcoidosis, Neurosarcoidosis, Lupus, Discoid Lupus, Lupus Pernio, Lupus Nephritis, Systemic Lupus Erythematosis (SLE), Asthma, Macular Degeneration, Uveitis, Crohn's, Irritable Bowel Syndrome, Sjogren's, Fibromyalgia, Chronic Fatigue Syndrom (CFS), Chronic Fatigue Immune Dysfunction Syndrome (CFIDS), Myalgic Encephalitis (ME), Amyotrophic Lateral Sclerosis (ALS), Parkinson's, Multiple Sclerosis, Autism Spectrum Disorder (ASD), Attention Deficit Disorder (ADD), and Attention Deficit Hyperactivity Disorder (ADHD). This invention achieves this by reducing the ability of the stealthy bacteria to produce proteins with their 70S Ribosome. The 30S and 50S subunits of the bacterial ribosome are targeted individually and collectively. Further, this invention reduces the availability of Angiotensin II to the host's Angiotensin receptors, conditioning the immune system to recognize and kill the bacteria. Finally, this invention reduces the availability of Angiotensin II and cytokines to the bacterial pathogens and thus inhibits the ability of their genome to scavenge (from a host patient) the amino acids, and other biochemicals necessary for bacterial survival.

24 Claims, No Drawings

(56) References Cited

OTHER PUBLICATIONS

Marshall, T. G. et al. (Aug. 22, 2002). "Remission in Sarcoidosis," *Clinical Medicine & Health Research*, located at <http://clinmed.netprints.org/cgi/content/full/2002080004>. (7 pages).

Marshall, T. G. et al. (Aug. 29, 2002). "Valsartan Dosing Regime Modulates Psychotic Events in Two Sarcoidosis Patients," *Clinical Medicine & Health Research*, located at <http://clinmed.netprints.org/cgi/content/full/2002080006>. (4 pages).

Marshall, T. G. et al. (Jan. 10, 2006). "Common Angiotensin Receptor Blockers May Directly Modulate the Immune System via VDR, PPAR and CCR2b," *Theoretical Biology and Medical Modelling*, 3(1):33 pages.

Marshall, T. G. et al. (Jan. 27, 2003). "New Treatments Emerge as Sarcoidosis Yields Up its Secrets," *Clinical Medicine & Health Research*, located at <http://clinmed.netprints.org/cgi/content/full/2003010001>. (10 pages).

Mercola, J. (Sep. 14, 2002). Study Summary for "Remission in Sarcoidosis" by Marshall, T. G. et al., located at <http://articles.mercola.com/sites/articles/archive/2002/09/14/sarcoidosis.aspx>. (2 pages).

Perez, T. (Sep. 10-14, 2008). Written transcript of "MP Study Results" presented at 6th International Congress on Autoimmunity, Porto, Portugal, located at <http://autoimmunityresearch.org/transcripts/ICA2008_Transcript_TomPerez.pdf>. (4 pages).

Proal, A. D. et al. (2009). "Autoimmune Disease in the Era of the Metagenome," *Autoimmunity Reviews*, Article in Press, 5 pages.

Proal, A. D. et al. (Submitted 2009). "Dysregulation of the Vitamin D Nuclear Receptor May Contribute to the Higher Prevalence of Some Autoimmune Diseases in Women," *Annals of the New York Academy of Sciences*, unedited manuscript, 16 pages.

Restriction Requirement mailed May 14, 2009, for U.S. Appl. No. 11/309,355, filed Jul. 31, 2006, 7 pages.

Autoimmunity Research Foundation (Last modified on Jul. 29, 2009). "Timeline of the Marshall Protocol," located at <http://mpkb.mp-dev.com/doku.php/home:arf:timeline> visited on Aug. 20, 2009.

Goldgerg et al. (2002). "New chemotherapy approaches in colorectal cancer," In *Colorectal Cancer, A clinical guide to therapy*. Harry Bleiberg et al. ed., 61, p. 629, and 632-633.

Rao et al. (1998). "Fixed-dose combination therapy: panacea or poison," *Intensive Care Med* 24:283-285.

Sotomayor et al. (1992). "Minocycline in combination with chemotherapy or radiation therapy in vitro and in vivo," *Cancer Chemother Pharmacol*, 30:377-384.

Teicher et al. (1996). "TNP-470/Minocycline/Cytotoxic Therapy: A Systems Approach to Cancer Therapy," *European Journal of Cancer*, 32A(14):2461-2466.

China Medicinal Biotech Forum 2009. "The VDR and Metastasizing Cancers," presented by Prof. Trevor Marshall. Autoimmunity Research Foundation, 8 pages.

WCG 2008 Presentation. "Understanding Human Disease requires study of a Metagenome, not just the Human Genome," presented by Prof. Trevor Marshall. Autoimmunity Research Foundation, 12 pages.

Wu et al. (Aug. 2009). "A human colonic commensal promotes colon tumorigenesis via activation of T helper type 17 T cell response," *Nature Medicine* (Advance Online Publication), pp. 1-8.

Shoman, M (Apr. 2001). "Could Antibiotics Cure Your Hashimoto's Disease?" located at <http://www.thyroid.about..com/cs/hashimotos/a/antibiotics.htm> (pp. 1-2).

"Understanding Lupus", Lupus Foundation of America, Inc., Retrieved on Jun. 4, 2010, Webpage available at: http://www.lupus.org/webmodules/webarticlesnet/templates/new_learnunderstanding.aspx?articleid=2231&zoneid=523.

Final Office Action received for U.S. Appl. No. 11/608,838, mailed on Jun. 10, 2010, 24 pages.

"Cancer Bacteria", From Wikipedia, the free encyclopedia, Retrieved on Mar. 10, 2010, Available at: http://en.wikipedia.org/wiki/Cancer_bacteria.

"Pathogenic bacteria", From Wikipedia, the free encyclopedia, Retrieved on Mar. 10, 2010, Available at: http://en.wikipedia.org/wiki/Pathogenic_bacteria.

Final Office Action received for U.S. Appl. No. 11/309,355, mailed on Mar. 16, 2010, 20 pages.

Gorbach, S. L., "The intestinal microflora and its colon cancer connection", Infection, vol. 10, No. 6, 1982, pp. 379-384.

"Alzheimer's-associated protein may be part of the innate immune system", Massachusetts General Hospital, Mar. 3, 2010, Webpage available at: http://www.sciencedaily.com/releases/2010/03/100302201656.htm.

Moore et al., "Intestinal floras of populations that have a high risk of colon cancer", Applied and Environmental Microbiology, vol. 61, No. 9 Sep. 1995, pp. 3202-3207.

Nicolson et al., "Role of Chronic Bacterial and Viral Infections in Neurodegenerative, Neurobehavioral, Psychiatric, Autoimmune and Fatiguing Illnesses: Part 1", British Journal of Medical Practitioners, vol. 2, No. 4, Dec. 2009, pp. 20-28.

Nicolson et al., "Role of Chronic Bacterial and Viral Infections in Neurodegenerative, Neurobehavioural, Psychiatric, Autoimmune and Fatiguing Illnesses: Part 2", British Journal of Medical Practitioners, vol. 3, No. 1, Mar. 2010, pp. 301-310.

Quigley Emma, "The vitamin D receptor and its role in inflammation and host defence: interview with Dr. Robert Modlin", Expert Opinion on Therapeutic Targets, vol. 11, No. 4, Apr. 2007, pp. 431-433.

Soscia et al., "The Alzheimer's Disease-Associated Amyloid β-Protein Is an Antimicrobial Peptide", PLoS One, vol. 5, No. 3, pp. 1-10, Mar. 2010.

Final Office Action received for U.S. Appl. No. 11/309,355, mailed on Oct. 16, 2013, 27 pages.

Non-Final Office Action received for U.S. Appl. No. 11/608,838, mailed on Jan. 31, 2014, 29 pages.

\* cited by examiner

US 8,865,749 B2

TREATMENT AND PREVENTION OF TH1 AND 'AUTOIMMUNE' DISEASES EFFECTED WITH ANTIBIOTICS AND/OR ANGIOTENSIN INHIBITION

BACKGROUND OF INVENTION

It is currently believed that the diseases known as "autoimmune" diseases are caused by the body's immune system attacking the body itself. But I have discovered that these so-called "autoimmune" diseases are actually caused by stealthy intra-cellular bacteria. I have discovered that the 'autoimmune' diseases form a subset of the class of inflammatory disease characterized by a Th1 cytokine profile, with an over-abundance of the secosteroid hormone 1,25-dihydroxyvitamin-D (1,25-D), being generated in the inflamed body tissue. This hormone is also a paracrine cytokine. Further, I have discovered that the Th1 diseases are caused by multiple species of very tiny L-form Cell-Wall-Deficient (CWD) antibiotic-resistant bacteria living within the cytoplasm of cells, including the phagocytic cells (monocytes, macrophages, lymphocytes, neutrophils and polymorphonuclear cells) of the immune system itself. These bacteria cause the cell nucleus to release the mRNA signaling the Th1 cytokine cascade, without the need for conventional signaling by, for example, CD4+ T-Lymphocytes.

SUMMARY OF INVENTION

This invention is a method of killing the stealthy intracellular bacteria which cause many Th1 and 'Autoimmune' diseases. The methods described in this invention will treat and prevent the diseases customarily named Diabetes Type 1, Diabetes Type 2, Rheumatic Arthritis, Reactive Arthritis, Osteo Arthritis, Psoriasis, Scieroderma, Osteoporosis, Atherosclerosis, Myocarditis, Endocarditis, Pericarditis, Alzheimer's, Cystic Fibrosis, Hashimoto's Thyroiditis, Graves Disease, Leprosy, Syphilis, Lyme, Chronic Lyme, Borreliosis, Neuro-borreliosis, Inflammatory Bowel Disease (IBD), Tuberculosis, Latent Tuberculosis, Sarcoidosis, Neurosarcoidosis, Lupus, Discoid Lupus, Lupus Pernio, Lupus Nephritis, Systemic Lupus Erythematosis (SLE), Asthma, Macular Degeneration, Uveitis, Crohn's, Irritable Bowel Syndrome, Sjogren's, Fibromyalgia, Chronic Fatigue Syndrom (CFS), Chronic Fatigue Immune Dysfunction Syndrome (CFIDS), Myalgic Encephalitis (ME), Amyotrophic Lateral Sclerosis (ALS), Parkinson's, Multiple Sclerosis, Autism Spectrum Disorder (ASD), Attention Deficit Disorder (ADD), and Attention Deficit Hyperactivity Disorder (ADHD).

This invention achieves this by reducing the ability of the stealthy bacteria to produce proteins with their 70S Ribosome. The 30S and 50S subunits of the bacterial ribosome are targeted both individually and collectively. Further, this invention reduces the availability of Angiotensin II to the host's Angiotensin receptors, conditioning the immune system to recognize and kill the bacterial pathogens. Finally, this invention reduces the availability of Angiotensin II and cytokines to the pathogens and thus inhibits the ability of their genome to scavenge (from a host patient) the amino acids, and other biochemicals necessary for bacterial survival.

Special Considerations for Asserted Therapeutic or Pharmacological Utilities

With respect to MPEP 21 07.03 "Special Considerations for Asserted Therapeutic or Pharmacological Utilities," the utility of this methods patent has been established by "statistically relevant data documenting the activity of a compound or composition, arguments or reasoning, documentary evidence (e.g., articles in scientific journals), or any combination thereof." A sampling of peer-reviewed papers and conference presentations sufficient to establish such utility, and which also document "actual evidence of success in treating humans," includes:

Marshall T G, Marshall F E: Sarcoidosis succumbs to antibiotics—implications for autoimmune disease. Autoimmunity Reviews, 2004; 3(4):295-3001.

Marshall T G, Fenter B, Marshall F E: Antibacterial Therapy Induces Remission in Sarcoidosis. Herald MKDTS 2004 g; Volume III: Release 1. (The Journal of the Interregional Clinical-Diagnostic Center, Kazan, published in Russian translation). Invited Paper. Special issue on Sarcoidosis. ISSN: 1726-6149

Marshall T G, Fenter B, Marshall F E: Putative Antibacterial Mechanisms for Angiotensin Receptor Blockers. JOIMR 2004;2(2):1.

Marshall T G, Marshall F E: Sarcoidosis succumbs to antibiotics—implications for autoimmune disease. Autoimmunity Reviews, 2004; Supplement 2:55 (Abstracts of 4th International Congress on Autoimmunity)

Marshall T G: Bacterial Th1 Processes Seem Key to Chronic Lyme Remission. ILADS conference, October 2004, Rye Town, N.Y.

Marshall T G: How Borrelia Evades the Immune System, and How we Help it Kill This Th1 Bacterium. '30$^{th}$ Anniversary of Lyme Disease' conference, Farmington, Conn., May 7, 2005

Marshall T G, Mangin M, Marshall F E: Bacterial Th1 Processes Key to CFS/ME Remission. AACFS conference, Madison, Wis., October 2004

Marshall T G: Genomics, Molecular Medicine and Antibiotic Resistance. 'Recovery From Chronic Disease' conference, Chicago, Ill., Mar. 12, 2005.

Th1 Inflammation

Th1 inflammation is often defined as inflammation which produces an inflammatory cytokine profile including significant Interferon-gamma. Moreover, since the Th1 cytokine release also induces the synthesis of the secosteroid hormone 1,25-dihydroxyvitamin-D (1,25-D) in the infected phagocytes, it is possible to measure the proportion of 1,25-D which leaches into the bloodstream, together with plasma 25-hydroxyvitamin-D (25-D), and estimate the extent of Th1 process in inflamed tissue.

One estimate of Th1 inflammation is performed by calculating the D-Ratio, the ratio of 1,25-D (in pg/ml) to the 25-D (in ng/ml). The value for a healthy population is 1.25, and this ratio is elevated in Th1 immune disease. This measurement and prediction is only valid if the patient is not taking any supplements containing Vitamin D, and the value of the presenting 25-D assay therefore is between 14 ng/ml and 20 ng/ml. See, for example:—Marshall T G, Marshall F E: Vitamin D maybe Harmful in Rheumatic Disease, Letter to editor 28700, BMJ, Jan 13, 2003. Available from URL http://bmj.bmjjournals.com/cgi/eletters/326/7379/12/b.

Many investigators have noted that the level of 25-D falls in patients with the Th1 diseases, but that observation has not heretofore been recognized as a marker for Th1 inflammatory disease. It has been mistakenly linked with an aberrant calcium metabolism. The calcium metabolism is, however, primarily regulated by the Para Thyroid Hormone (PTH) and the calcium-sensing receptor (CASR). See, for example: Thakker R V: *Disorders of the calcium-sensing receptor*. Biochim Biophys Acta. 1998 Dec. 10; 1448(2): 166-70.

For the purpose of this specification and claims, the term 'Th1 Disease' will be used to denote a disease characterized by inflammation involving intra-cellular bacterial pathogens and/or the presence of a dysregulated Vitamin-D metabolism.

Th1 Diseases

The Th1 inflammatory diseases are customarily named Diabetes Type 1, Diabetes Type 2, Rheumatic Arthritis, Reactive Arthritis, Osteo Arthritis, Psoriasis, Scieroderma, Osteoporosis, Atherosclerosis, Myocarditis, Endocarditis, Pericarditis, Alzheimer's, Cystic Fibrosis, Hashimoto's Thyroiditis, Graves Disease, Leprosy, Syphilis, Lyme, Chronic Lyme, Borreliosis, Neuro-borreliosis, Inflammatory Bowel Disease (IBD), Tuberculosis, Latent Tuberculosis, Sarcoidosis, Lupus, Discoid Lupus, Lupus Pernio, Lupus Nephritis, Systemic Lupus Erythematosis (SLE), Asthma, Macular Degeneration, Uveitis, Crohn's, Irritable Bowel Syndrome, Sjogren's, Fibromyalgia, Chronic Fatigue Syndrom (CFS), Chronic Fatigue Immune Dysfunction Syndrome (CFIDS), Myalgic Encephalitis (ME), Amyotrophic Lateral Sclerosis (ALS), Parkinson's, Multiple Sclerosis, Autism Spectrum Disorder (ASD), Attention Deficit Disorder (ADD), and Attention Deficit Hyperactivity Disorder (ADHD).

Many of these diseases are often described as "Autoimmune" diseases. It is currently believed that the diseases known as "autoimmune" diseases are caused by the body's immune system attacking the body itself. I have discovered that the 'autoimmune' diseases form a subset of the class of disease characterized by a Th1 cytokine profile, with an overabundance of the secosteroid hormone 1,25-D being generated in the inflamed body tissue, and/or a reduction in the level of systemic 25-D caused by hyper-active conversion to 1,25-D in the inflamed tissues.

I have discovered that these Th1 diseases, including the so-called "autoimmune" diseases, are actually caused by occult intra-cellular bacteria. Tiny bacteria, dozens of them, can live within a single phagocyte. They live within the cytoplasm of the phagocyte, from whence they activate, and/or simulate, NuclearFactor-kappaB to signal the Nucleus to release a 'messenger Ribo Nucleic Acid' (mRNA), allowing transcription of the cytokines characteristic of the Th1 immune reaction.

The bacteria directly cause the nucleus to release mRNA signaling the Th1 cytokine cascade, without the need for conventional signaling by CD4+ T-Lymphocytes, which play no significant role in signaling the release of cytokines causing the Th1 inflammatory reaction (although some of the T-cells will also be parasitized by pathogens, and those will directly participate in the cytokine release).

Our recent paper in "Autoimmunity Reviews" describes this process in more detail, and also describes a mechanism whereby a Th1 disease can be identified as such: Marshall T G, Marshall F E: *Sarcoidosis succumbs to antibiotics-implications for autoimmune disease*. Autoimmun. Rev. 2004 June;3(4):295-300.

This invention is a method of killing the intra-cellular bacteria which cause the Th1 diseases, by using a novel regimen of antibiotics, and/or a novel antibiotic dosing regimen, to condition the immune system to recognize and kill the bacterial pathogens. This invention also (optionally) functions by simultaneously reducing the level of Angiotensin II available to pathogens and the inflamed tissue.

Subsequent to the long-term administration of the therapy described in this invention, Th1 diseases, including the diseases currently though to be 'autoimmune', are prevented and/or put into remission.

Optimally Effective Antibiotics and Dosing Regimes

Most of the above Th1 diseases are idiopathic. This idiopathic nature demonstrates that this invention is not obvious, since the bacterial pathogenesis for these diseases has remained elusive, and effective treatments have not been hitherto invented.

These bacteria are so very small they have shed parts of their physical structure (their Cell Walls) and possibly also some of their plasmids, in the transformation into the L-form pathogens. Therefore, analysis of the actions of antibiotics on these organisms can only be performed after analysis of the bacterial genome. These L-form bacteria are very, very, difficult to culture, and standard antibiotic sensitivity testing offers little or no help in understanding this invention.

Standard antibiotic regimes do not kill these intra-phagocytic bacteria. They may therefore be thought of as "antibiotic resistant" bacteria. As CWD bacteria they are not susceptible to antibiotics in most common use, the 'bactericidal' antibiotics.

This invention can kill these antibiotic-resistant bacteria. One problem is that as the bacteria are killed they release endotoxins, and/or other toxic biochemicals, into the cytoplasm, causing further disease symptoms, sometimes of even higher intensity than during the actual activity of the Th1 disease itself. This can be likened to the jarisch-Herxheimer Reaction which has been documented when killing bacterial pathogens, most notably when killing the *Treponema pallidum* which are believed to cause Syphilis.

This invention solves the problem of Herxheimer-induced anaphylaxis by targeting the bacterial genome—carefully controlling the pathogen's environment, as well as the antibiotic selection and dosing regimens.

Even if the patient is given a conventional dosage of the same antibiotics described in this invention, the antibiotics may fail to totally kill the pathogens, and if they do, there is the risk of a cytokine release sufficiently intense to cause life-threatening cardiac bradycardia or life-threatening pulmonary insufficiency, both of which were observed during experimentation with this invention.

This inventor has previously performed research on novel drug-dosing regimes in several diseases. In Diabetes I explored increased efficacy and reduced side-effects from a continuous infusion of Insulin, and in Cryptorchidism and Infertility I explored increased efficacy of pulsatile dosing of the hormones LH-RH and Gn-RH.

One of the best ways to administer a continuous concentration of any drug is by using an infusion pump, like the transcutaneous infusion pump for Insulin I invented in 1982: Marshall T G, Mekhiel N, Jackman W S, Perlman K, Albisser A M: *New microprocessor-based insulin controller*. IEEE Trans Biomed Eng. 1983 November;30(11):689-95.

During my Doctoral Research we also explored pulsatile administration of drugs, and my research group was able to cure Cryptorchidism and Infertility by using pulsatile injections of hormone, rather than using a continuous concentration: Keogh E J, MacKellar A, Mallal S A, Dunn A G, McColm S C, Somerville C P, Glatthaar C, Marshall T, Attikiouzel J: *Treatment of cryptorchidism with pulsatile luteinizing hormone-releasing hormone (LH-RH)*. J Pediatr Surg. 1983 June; 18(3):282-3.

It is typically believed that antibiotics administered at doses below the Minimum Inhibitory Concentration (MIC) are ineffective, and are likely to encourage the formation of antibiotic-resistant forms of the bacteria. However, when killing the antibiotic-resistant intra-cellular bacterial L-forms which cause the Th1 diseases, I have discovered that antibiotics blocking bacterial protein synthesis by inhibiting the function of the 70S bacterial Ribosome are needed, and I have moreover discovered they are often optimally effective when delivered in a pulsatile fashion, wherein the peak concentration in the bloodstream may or may not be in excess of the MIC, but where the antibiotic concentration is allowed to decay away to a lower value before the next dose of antibiotic is given.

It should be noted that the simplified pharmacokinetic model which is usually used to describe antibiotic absorption, anticipates an exponential rise of concentration to the peak value, and then a single exponential decay of that concentration (which is considered to be distributed within the plasma compartment). A pseudo-continuous concentration in the bloodstream can be achieved by dosing the drug at sufficient frequency that the next dose is absorbed before significant exponential decay from the previous dose.

The claimed methods have been successfully tested with several hundred human subjects.

The 70S Bacterial Ribosome

These stealthy bacteria synthesize proteins (which they need for their survival) within a structure called a Ribosome. The bacterial ribosome is termed a '70S Ribosome' and, for the sake of easy analysis, it is conventionally divided into two subunits called the '30S' and the '50S' subunits.

The function of the 30S subunit is primarily determined by the 16S RNA of which it is primarily comprised, while the 50S subunit's function is primarily determined by the bacterial 23S RNA. Both subunit structures are completed by a variety of proteins and additional smaller RNA elements.

Antibiotics which inhibit the 30S subunit typically bind in the region near the helix which 'advances' during the transcription of bacterial mRNA to bacterial proteins. Antibiotics which inhibit the 50S subunit typically bind in the region where the tRNA docks, or in the region termed the Peptidyl Transferase Center (PTC), or in the region where the partially assembled protein travels through the rest of the 50S subunit, prior to emerging from the ribosome.

The effectiveness of this invention is partially due to its control of the bacterial environment, and partially due to the use of antibiotics which act symbiotically in different areas of the ribosome, reducing the statistical likelihood that any bacteria species will have developed resistance mechanisms which simultaneously overcome all the methods being used by this invention to weaken the function of the ribosome.

Intra-Cellular Bacteria need 'Nutrition' for their Survival

The genomes of two of the Th1 pathogens have been closely studied. Both *Treponema* and *Borrelia* bacteria are among the species which 'team up' to cause the Th1 diseases. They are both capable of existing in a number of Cell Wall Deficient (CWD) or 'L-forms' and can flourish in tiny coccoids down to sub-microscopic sizes.

These bacteria have been photographed by electron microscopy in an intra-cellular coccoid form down to 0.015 microns in diameter, which is smaller than is visible in an optical microscope. They can also form clusters, and colonies, which are much larger, and the spirochetal form, which is most commonly known, is 100 or more times the surface area of the smallest intra-cellular L-forms.

In general, these L-forms do not appear in laboratory cultures. Indeed, *Treponema pallidum* is almost impossible to culture in-vitro, although it can be cultured if body-fluids are judiciously added to the gels. It is a good example of an "occult" or "stealthy" pathogen—one that does not appear in standard laboratory cultures, and therefore a 'stealthy infection' which can easily proliferate unchecked, and cause chronic disease.

The genomes of both *Treponema* and *Borrelia* show that lipid biosynthesis is lacking, and they scavenge nourishment from the host. Energy production is primarily via an anaerobic glycolytic pathway, rather than the usual NADPH-providing pentose phosphate pathway. Both have to scavenge amino acids, fatty acids and enzyme cofactors from the host. Angiotensin II is a rich source of amino acids (containing 8 of them in an easily-cleaved structure).

I have discovered that suppression of Angiotensin II from binding to receptors in the inflamed tissue exerts a powerful antibacterial action, in addition to enabling the immune system to more effectively recognize the pathogens. Although the above is one pathway for this antibacterial action, more are described in our paper Marshall T G, Fenter B, Marshall F E: Putative Antibacterial Mechanisms for Angiotensin Receptor Blockers. JOIMR 2004;2(2):1.

Common drugs, such as the Angiotensin Receptor Blockers (ARBs), are capable of significantly weakening the defensive mechanism of the intra-cellular bacteria. However, the administration of these ARBs at intervals beyond about 10 hours causes them to lose efficacy, because the concentration in the blood stream drops below the level at which a complete angiotensin blockade is effected. Thus, the conventional dosing of these ARBs that the FDA approved for hypertension, 24 hourly, with "the amount of return on twice daily dosing . . . already a poor investment," does not allow them to function effectively for weakening stealthy bacteria. They must be dosed much more frequently (preferably semi-continuously) so as to apply the maximum possible blockade to the Angiotensin Receptors in the inflammation, a blockade which reduces the availability of Angiotensin II to both the inflamed tissue and the pathogens. This is one of the novel elements in this invention.

A chemical or biologic agent which acts as a transcriptase inhibitor of Angiotensin, inhibiting the ability of the body to generate either Angiotensin I and/or Angiotensin II through Ribo Nucleic Acid (RNA) transcription, would perform the same function as the ARBs, and reduce the availability of Angiotensin II to the inflamed tissue, and the use of such chemicals or agents are also part of this invention.

Other agents, including Angiotensin Converting Enzyme Inhibitors (ACEI) reduce the supply of Angiotensin II to the inflamed tissue, and the use of ACEI to reduce the supply of Angiotensin II to the inflamed tissue are also part of this invention.

Prior Art

Patent Publication 20050112638, dated May 26, 2005, starts "The renin-angiotensin system ("RAS") plays an integral role in maintaining vascular tone, optimal salt and water homeostasis, and cardiac function in humans." There is no disclosure of Angiotensin having any effect on bacteria, nor of bacteria being responsible for inflammation, or, indeed, any Th1 disease. This patent application is not relevant prior art.

Patent Publication 20040097565, dated May 20, 2004, includes claim 30 "An use of a compound having the angiotensin II antagonistic activity selected from Candesartan, Telmisartan, Olmesartan and Tasosartan, a prodrug thereof or a salt thereof for preparation of an antiinflammatory agent." There is no disclosure of the ARB having any effect on bacteria, nor of stealthy bacteria being responsible for inflammation, or being responsible for atherosclerosis. There is no disclosure of antibiotics which inhibit the protein synthesis by the 70S bacterial ribosome, or to any symbiosis between ARBs and such antibiotic actions. This patent application is not relevant prior art.

Patent Application 20030199424, dated Oct. 23, 2003, "The present invention is directed to the use of angiotensin II receptor I (AT.sub.1 receptor) antagonists for the treatment, prophylaxis, reversal and/or symptomatic relief of a neuropathic condition, especially a peripheral neuropathic condition such as painful diabetic neuropathy." There is no disclosure of the ARB having any effect on bacteria, nor of stealthy bacteria being responsible for inflammation, or Neurosarcoidosis or Neuroborreliosis. There is no disclosure of the effect on neuropathic conditions of antibiotics which inhibit the protein synthesis by the 70S bacterial ribosome, or to any symbiosis between ARBs and such antibiotic actions. This patent application is not relevant prior art.

Prior Art possibly includes US PTO Provisional Patent Application No. 60/310,064 filed Aug. 6, 2001, "A Method to Delay the Progression of a Number of Current Diseases". That provisional patent application (which may have been abandoned) canvasses the use of Angiotensin Converting Enzyme Inhibitors (ACEI) in the treatment of viruses and viral diseases. It must be noted that Ser. No. 60/310,064 does not relate to the bacterial pathogenesis we have discovered, nor does it anticipate any unified pathogenesis of the inflammatory diseases. This provisional patent application is not relevant prior art. Because Ser. No. 60/310,064 has not accurately disclosed the underlying pathogenesis, or the underpinning genomics, the improvement in patient health with the method disclosed in Ser. No. 60/310,064 does not approximate what is achieved by this invention which in the disclosed implementations is already returning hundreds of desperately ill patients to full health.

Conclusion

It will be clear that the invention may be practiced otherwise than as particularly described in the foregoing description and examples. Numerous modifications and variations of the present invention are possible in light of the above teachings and, therefore, are within the scope of the appended Claims.

What is claimed is:

1. A method for treating symptoms of an autoimmune disease caused by intra-cellular bacterial pathogens, comprising administering to a subject in need thereof a therapeutically effective amount of Olmesartan or Olmesartan medoxomil; optionally with one or more antibiotics capable of inhibiting bacterial protein synthesis by inhibiting the intra-cellular bacterial 70S-bacterial-ribosome to treat intra-cellular bacterial pathogens and to treat symptoms of the autoimmune disease, wherein the Olmesartan or Olmesartan medoxomil is administered by intermittent administration in such a way that the Olmesartan or Olmesartan medoxomil has a concentration in the subject's bloodstream that is constrained from falling below 40% of its peak value, and wherein the Olmesartan or Olmesartan medoxomil is administered in a range of between 10 mg and 40 mg every 3 to 10 hours.

2. The method of claim 1, wherein the autoimmune disease is not Sarcoidosis or Neurosarcoidosis.

3. The method defined in claim 1 wherein the intermittent administration is selected from the group consisting of oral dosing at intervals sufficiently small to stabilize the Olmesartan or Olmesartan medoxomil level between 40% and 100% of its peak value, injections at intervals sufficiently small to stabilize the Olmesartan or Olmesartan medoxomil level between 40% and 100% of its peak value, intermittent intravenous administration at intervals sufficiently small to stabilize the Olmesartan or Olmesartan medoxomil level between 40% and 100% of its peak value, and trans-cutaneous infusion at intervals sufficiently small to stabilize the Olmesartan or Olmesartan medoxomil level between 40% and 100% of its peak value.

4. The method defined in claim 2 wherein the 70S ribosome-inhibiting-antibiotic comprises a 30S Bacterial Ribosomal subunit inhibitor selected from the group consisting of Minocycline, Minocycline hydrochloride, Demeclocycline, Demeclocycline hydrochloride, Tigecycline, Tetracycline, Oxytetracycline, Doxycycline, Doxycycline hyclate, Spectinomycin, Hygromycin, Paromomycin, Streptomycin, Kanamycin, Gentamicin, Tobramycin, Amikacin, Netilmicin, and Neomycin.

5. The method defined in claim 4 wherein the 30S Bacterial Ribosomal subunit inhibitor antibiotic is administered with a pulsatile dosing frequency between once every 36 hours and once every 72 hours, such that the concentration of the antibiotic in plasma is allowed to drop below the minimum inhibitory concentration before the next dose of antibiotic is administered.

6. The method defined in claim 1 wherein the 70S bacterial-ribosome-inhibiting antibiotic comprises a 50S Bacterial Ribosomal subunit inhibitor selected from the group consisting of Azithromycin, Chloramphenicol, Linezolid, Erythromycin, Roxithromycin, Troleandomycin, Tylocin, Carbomycin A, Clindamycin, Lincomycin, Cethromycin, Telithromycin, Sparsomycin, Tiamulin, Dalfopristin, and Quinupristin.

7. The method defined in claim 6 wherein the 50S Bacterial Ribosomal subunit inhibitor antibiotic is administered with a pulsatile dosing frequency between once every 36 hours and once every 21 days, such that the concentration of the antibiotic in plasma is allowed to drop below the minimum inhibitory concentration before the next dose of antibiotic is administered.

8. The method defined in claim 1 wherein the 70S bacterial-ribosome is inhibited by two or more antibiotics selected so that both the 30S and 50S subunits are symbiotically inhibited from full bacterial protein synthesis.

9. The method defined in claim 8 wherein the 70S ribosome is inhibited by one 30S subunit inhibiting antibiotic selected from the group consisting of Minocycline, Minocycline hydrochloride, Demeclocycline, Demeclocycline hydrochloride, Tigecycline, Tetracycline, Oxytetracycline, Doxycycline, Doxycycline hyclate, Spectinomycin, Hygromycin, Paromomycin, Streptomycin, Kanamycin, Gentamicin, Tobramycin, Amikacin, Netilmicin, and Neomycin; together with one or more 50S subunit inhibiting antibiotics selected from the group consisting of Azithromycin, Clarithromycin, Clindamycin, Chloramphenicol, Linezolid, Erythromycin, Roxithromycin, Troleandomycin, Tylocin, Carbomycin A, Sparsomycin, Lincomycin, Cethromycin, Telithromycin, Tiamulin, Dalfopristin, and Quinupristin.

10. The method defined in claim 8 wherein the 70S ribosome is inhibited by one 30S subunit inhibiting antibiotic selected from the group consisting of Minocycline, Minocycline hydrochloride, Demeclocycline, Demeclocycline hydrochloride, Tigecycline, Tetracycline, Oxytetracycline, Doxycycline, and Doxycycline hyclate; and one or more 50S subunit inhibiting antibiotics selected from the group consisting of Azithromycin, Erythromycin, Roxithromycin, Troleandomycin, Tylocin, Carbomycin A, and Telithromycin.

11. The method defined in claim 8 wherein some, or all, of the antibiotics are administered with a pulsatile dosing frequency between once every 36 hours and once every 21 days, so that the concentration of the antibiotic in plasma is allowed to drop below the minimum inhibitory concentration before the next dose of antibiotic is administered.

12. The method defined in claim 1 wherein the one or more 70S bacterial-ribosome-inhibiting antibiotics comprise one 30S ribosomal sub-unit inhibiting antibiotic selected from the group consisting of Minocycline, Minocycline hydrochloride, Demeclocycline, and Demeclocycline hydrochloride;

together with Azithromycin 50S subunit inhibiting antibiotic; wherein the 30S ribosomal sub-unit inhibitor is administered at a frequency between 36 hours and 8 days; and wherein the Azithromycin is administered at a frequency between 6 days and 21 days.

13. A method for treating symptoms of an autoimmune disease caused by intra-cellular bacterial pathogens, comprising administering to a subject in need thereof a therapeutically effective amount of Olmesartan or Olmesartan medoxomil; together with one or more antibiotics capable of inhibiting bacterial protein synthesis by inhibiting the intracellular bacterial 70S-bacterial-ribosome to treat intra-cellular bacterial pathogens and to treat symptoms of the autoimmune disease, wherein the Olmesartan or Olmesartan medoxomil is administered by intermittent administration in such a way that the Olmesartan or Olmesartan medoxomil has a concentration in the subject's bloodstream that is constrained from falling below 40% of its peak value, and wherein the Olmesartan or Olmesartan medoxomil is administered in a range of between 10 mg and 40 mg every 3 to 10 hours.

14. The method defined in claim 13 wherein the 70S bacterial-ribosome-inhibitor is an antibiotic selected from the group consisting of Minocycline, Minocycline hydrochloride, Demeclocycline, Demeclocycline hydrochloride, Tigecycline, Tetracycline, Oxytetracycline, Doxycycline, Doxycycline hyclate, Spectinomycin, Hygromycin, Paromomycin, Streptomycin, Kanamycin, Gentamicin, Tobramycin, Amikacin, Netilmicin, Neomycin, Azithromycin, Clindamycin, Chloramphenicol, Linezolid, Erythromycin, Roxithromycin, Troleandomycin, Tylocin, Sparsomycin, Carbomycin A, Sparsomycin, Lincomycin, Cethromycin, Telithromycin, Tiamulin, Dalfopristin, and Quinupristin.

15. A method for treating symptoms of an autoimmune disease caused by intra-cellular bacterial pathogens, comprising administering to a subject in need thereof a therapeutically effective amount of Olmesartan or Olmesartan medoxomil; optionally with one or more antibiotics capable of inhibiting bacterial protein synthesis by inhibiting the intracellular bacterial 70S-bacterial-ribosome to treat intra-cellular bacterial pathogens and to treat symptoms of the autoimmune disease, wherein the one or more antibiotics are provided in an amount below the Minimum Inhibitory Concentration, and wherein the Olmesartan or Olmesartan medoxomil is administered by intermittent administration in such a way that the Olmesartan or Olmesartan medoxomil has a concentration in the subject's bloodstream that is constrained from falling below 40% of its peak value, and wherein the Olmesartan or Olmesartan medoxomil is administered in a range of between 10 mg and 40 mg every 3 to 10 hours.

16. The method defined in claim 15 wherein one antibiotic is selected from a group of 30S subunit inhibiting antibiotics consisting of Minocycline, Minocycline hydrochloride, Demeclocycline, Demeclocycline hydrochloride, Tigecycline, Tetracycline, Oxytetracycline, Doxycycline, Doxycycline hyclate, Spectinomycin, Hygromycin, Paromomycin, Streptomycin, Kanamycin, Gentamicin, Tobramycin, Amikacin, Netilmicin and Neomycin; and one or more antibiotic(s) are selected from either or both of the following symbiotic groups: a group of 50S subunit-inhibiting-antibiotics consisting of Azithromycin, Erythromycin, Roxithromycin, Troleandomycin, Tylocin, Carbomycin A, Sparsomycin, Cethromycin, Telithromycin and Quinupristin; a group of 50S subunit-inhibiting-antibiotics which bind near the PTC, consisting of Clindamycin, Dalfopristin, Chloramphenicol, Linezolid, Tiamulin, and Lincomycin.

17. The method described in claim 15, wherein the one or more 70S bacterial-ribosome-inhibiting antibiotics comprise a 30S subunit inhibiting antibiotic administered with a pulsatile dosing frequency between once every 36 hours and once every 8 days, such that the concentration of the antibiotic in plasma remains below the minimum inhibitory concentration before the next dose of antibiotic is administered.

18. The method described in claim 15 where the period of treatment is 7 months or longer.

19. The method described in claim 1, wherein the autoimmune disease is selected from the group consisting of Diabetes Type 1, Diabetes Type 2, Rheumatic Arthritis, Reactive Arthritis, Osteo Arthritis, Psoriasis, Scleroderma, Osteoporosis, Hashimoto's Thyroiditis, IBD, Lupus, SLE, Asthma, Uveitis, Crohn's, Sjogren's, Multiple Sclerosis, ADHD, Parkinson's, and ALS.

20. The method described in claim 13, wherein the autoimmune disease is selected from the group consisting of Diabetes Type 1, Diabetes Type 2, Rheumatic Arthritis, Reactive Arthritis, Osteo Arthritis, Psoriasis, Scleroderma, Osteoporosis, Hashimoto's Thyroiditis, IBD, Lupus, SLE, Asthma, Uveitis, Crohn's, Multiple Sclerosis, ADHD, Parkinson's, and ALS.

21. The method described in claim 15, wherein the autoimmune disease is selected from the group consisting of Diabetes Type 1, Diabetes Type 2, Rheumatic Arthritis, Reactive Arthritis, Osteo Arthritis, Psoriasis, Scleroderma, Osteoporosis, Hashimoto's Thyroiditis, IBD, Lupus, SLE, Asthma, Uveitis, Crohn's, Multiple Sclerosis, ADHD, Parkinson's, and ALS.

22. The method described in claim 1, wherein the Olmesartan or Olmesartan medoxomil is administered at intervals of approximately 6 hours.

23. The method described in claim 13, wherein the Olmesartan or Olmesartan medoxomil is administered at intervals of approximately 6 hours.

24. The method described in claim 15, wherein the Olmesartan or Olmesartan medoxomil is administered at intervals of approximately 6 hours.

* * * * *